US006114284A

United States Patent [19]
Fujisawa et al.

[11] Patent Number: 6,114,284

[45] Date of Patent: Sep. 5, 2000

[54] GROWTH REGULATOR FOR CROP PLANTS AND METHOD FOR REGULATING THE GROWTH OF CROP PLANTS

[75] Inventors: Hiroshi Fujisawa, Kawasaki; Nada Morishige, Tokyo; Yasuo Kamuro, Ichinomiya, all of Japan

[73] Assignee: Nippon Zeon Co., Ltd., Tokyo, Japan

[21] Appl. No.: 09/125,789

[22] PCT Filed: Feb. 28, 1997

[86] PCT No.: PCT/JP97/00616

§ 371 Date: Feb. 25, 1999

§ 102(e) Date: Feb. 25, 1999

[87] PCT Pub. No.: WO97/31536

PCT Pub. Date: Sep. 4, 1997

[30] Foreign Application Priority Data

Feb. 28, 1996 [JP] Japan .................................... 8-067267

[51] Int. Cl.$^{7}$ ............................ A01N 37/42; A01N 43/12

[52] U.S. Cl. .......................... 504/140; 504/297; 504/312; 504/313

[58] Field of Search .................................... 504/312, 313, 504/140, 297

[56] References Cited

U.S. PATENT DOCUMENTS 3,821,864 7/1974 Stottlemyer ................................ 71/86
5,776,860 7/1998 Kamuro et al. ......................... 504/313

*Primary Examiner*—S. Mark Clardy
*Attorney, Agent, or Firm*—Armstrong, Westerman, Hattori, McLeland & Naughton

[57] ABSTRACT

A plant growth regulator comprising as the active ingredients gibberellin and a jasmonic acid ester represented by the following formula (1):

(1)

O, $R^1$, $COOR^2$ wherein $R^1$ and $R^2$ represent hydrocarbon groups. Gibberellin and the jasmonic acid ester are applied as a mixture, or as single agents each containing one of the two compounds, which are applied concurrently, or separately by a procedure wherein, while the earlier applied one is still in force, the other is applied.

20 Claims, No Drawings

GROWTH REGULATOR FOR CROP PLANTS AND METHOD FOR REGULATING THE GROWTH OF CROP PLANTS

TECHNICAL FIELD

This invention relates to a gibberellin-containing plant growth regulator exhibiting an enhanced gibberellin activity, and a method of regulating plant growth

BACKGROUND ART

Gibberellins are known as a plant growth regulator. Their plant growth regulating activities include, for example, seedless fruitage, maturation period acceleration and fruit enlargement of grape; fruit drop control for persimmon, navel orange and others; growth and development acceleration of Mituba (Cryptotaenia japonica MAKINO), spinach, Japanese butterbur and others; acceleration of growth and development of Udo salad plant (Aralia eordata THIMB) and others by breaking of dormancy; prevention of production of puffy tomato and others; fruit enlargement of cucumber and others; enhancement of number of set fruits of strawberries and others; and bloom acceleration of tulip, cyclamen and other flowers and ornamental plants.

Although gibberellin have various activities as mentioned above, its application is limited because it is expensive and must be applied to crops at a high concentration.

To obviate the difficulties of gibberellin, great progress is being made in development of synergists. For example, plant growth regulators having the following synergists have been proposed: parachlorophenoxyacetic acid (Japanese Examined Patent Publication (hereinafter abbreviated to "JP-B") S57-11281), cyclic-3',5'-adenylic acid (JP-B S57-15726), tryptophan (JP-B S58-27245), streptomycin (JP-B S60-39325), 6-benzyladenine (JP-B S61- 15044), choline (JP-B H5-78522), pyrazole compounds (Japanese Unexamined Patent Publication (hereinafter abbreviated to "JP-A") H4-199104) and abscisic acid (JP-A H5-139912). Most of the proposed plant growth regulators still have problems such that gibberellin must be applied at a high concentration, e.g., 100 ppm, for seedless fruitage and fruit enlargement of grapes, and the effect of plant growth regulation is not satisfactory.

Jasmonic acid esters represented by the general formula (1), below, are known compounds, which are described in WO94/18833. It is reported that the jasmonic acid esters have activities such as coloring improvement and sweetness enhancement of fruits of grape; growth and development acceleration of potatoes, rice, wheat and others; and fruit enlargement of strawberry, tomato and others. However, the activities of the jasmonic acid esters as observed when they are used alone, are not satisfactory for some crops.

DISCLOSURE OF THE INVENTION

To solve the problems of the prior art, the inventors made extensive researches, and found that the amount of gibberellin can be reduced as described in Plant Hormone Handbook (I), page 15, published by Baifukan, Japan, by the combined use of gibberellin with specified jasmonic acid esters, and further found that gibberellin and the jasmonic acid ester synergistically act for the effects of plant growth regulation such as growth and development acceleration, fruit enlargement, seedless fruitage, and germination acceleration, which effects cannot be obtained with the single use of these active ingredients. Based on these findings, the present invention has been completed.

In accordance with the present invention, there is provided a plant growth regulator which comprises, as active ingredients, gibberellin and a jasmonic acid ester represented by the general formula (1):

(1)

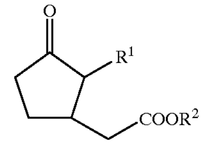

wherein each of $R^1$ and $R^2$ represents a hydrocarbon group, at a ratio (gibberellin/jasmonic acid ester) of 1/0.001 to 1/1,000,000 by weight.

Further, in accordance with the present invention, there is provided a method of regulating growth of a plant which comprises applying to crops gibberellin and a jasmonic acid ester represented by the above general formula (1) in combination. The combined application of gibberellin and the jasmonic acid ester can be effected either by a procedure of applying a mixture of these two active ingredients, or by a procedure of applying separately the two active ingredients, i.e., a procedure wherein, while the earlier applied one is still effective, the other is applied.

BEST MODE FOR CARRYING OUT THE INVENTION

Plant Growth Regulator

The gibberellin used in the present invention is not particularly limited and those which are generally used for ordinary plant growth regulators can be used. More than 80 varieties of gibberellins have heretofore been found, and are named in the order of discovery as gibberellin $A_1$, gibberellin $A_2$, gibberellin $A_3$ (hereinafter abbreviated to "$GA_3$"), gibberellin $A_4$ (hereinafter abbreviated to "$GA_4$"), and the like. Any of these gibberellins can be used in the present invention. Structural formulae of $GA_3$ and $GA_4$, which are typical examples of the gibberellins, are as follows $GA_3$

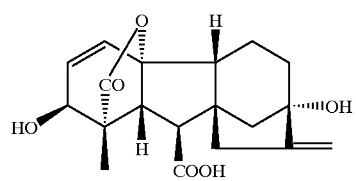

-continued

GA$_4$

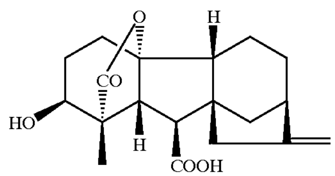

These gibberellins may be used either alone or as a combination of at least two thereof.

The jasmonic acid esters used in the present invention are represented by the above-mentioned general formula (1).

$R^1$ in the formula (1) represents a hydrocarbon group, preferably an alkyl group and an alkenyl group. The number of carbon atoms in $R^1$ is not particularly limited, but is usually in the range of 1 to 20, preferably 1 to 10, more preferably 2 to 8 and most preferably 3 to 6.

As examples of $R^1$, there can be mentioned methyl, ethyl, n-propyl, isopropyl, n-butyl, sec-butyl, t-butyl, n-pentyl, isopentyl, 2-methylbutyl, 1-methylbutyl, n-hexyl, isohexyl, 3-methylpentyl, 2-methylpentyl, 1-methylpentyl, n-heptyl, isoheptyl, n-octyl, isooctyl, 2-ethylhexyl, nonyl, decyl, allyl, 2-butenyl, 3-butenyl, isobutenyl, 4-pentenyl, 3-pentenyl, trans-2-pentenyl, cis-2-pentenyl, 1-pentenyl, 3-methyl-2-pentenyl, 5-hexenyl, 3-hexenyl, 2-hexenyl, heptenyl, octenyl, nonenyland decenyl groups. Of these, ethyl, n-propyl, isopropyl, n-butyl, sec-butyl, t-butyl, n-pentyl, isopentyl, 2-methylbutyl, 1-methylbutyl, n-hexyl, isohexyl, 3-methylpentyl, 2-methylpentyl, 1-methylpentyl, allyl, 2-butenyl, 3-butenyl, isobutenyl, 4-pentenyl, 3-pentenyl, trans-2-pentenyl, cis-2-pentenyl, 1-pentenyl, 3-methyl-2-pentenyl, 5-hexenyl, 3-hexenyl and 2-hexenyl groups are preferable. n-Pentyl, isopentyl, 2-methylbutyl, 1-methylbutyl, 4-pentenyl, 3-pentenyl, trans-2-pentenyl, cis-2-pentenyl and 1-pentenyl are especially preferable.

$R^2$ in the formula (1) represents a hydrocarbon group, preferably an alkyl group. The number of carbon atoms in $R^2$ is not particularly limited, but is usually in the range of 1 to 20, preferably 2 to 10, more preferably 2 to 8 and most preferably 3 to 4.

As examples of $R^2$, there can be mentioned methyl, ethyl, n-propyl, isopropyl, n-butyl, sec-butyl, t-butyl, n-pentyl, isopentyl, 2-methylbutyl, 1-methylbutyl, n-hexyl, isohexyl, 3-methylpentyl, 2-methylpentyl, 1-methylpentyl, n-heptyl, isoheptyl, n-octyl, isooctyl, 2-ethylhexyl, nonyl and decyl groups. Of these, ethyl, n-propyl, isopropyl, n-butyl, sec-butyl, t-butyl, n-pentyl, isopentyl, 2-methylbutyl, 1-methylbutyl, n-hexyl, isohexyl, 3-methylpentyl, 2-methylpentyl and 1-methylpentyl are preferable. n-Propyl, isopropyl, n-butyl, sec-butyl and t-butyl are especially preferable.

As specific examples of the jasmonic acid ester, there can be mentioned methyl (2-pentyl-3-oxo-cyclopentyl)acetate, methyl (2-(3-pentenyl)-3-oxo-cyclopentyl)acetate, ethyl (2-pentyl-3-oxo-cyclopentyl)acetate, ethyl (2-(2-pentenyl)-3-oxo-cyclopentyl)acetate, propyl (2-pentyl-3-oxo-cyclopentyl)acetate, propyl (2-(2-pentenyl)-3-oxo-cyclopentyl)acetate, propyl (2-(3-pentenyl)-3-oxo-cyclopentyl)acetate, propyl (2-(2-methylbutyl)-3-oxo-cyclopentyl)acetate, propyl (2-(2,2-dimethylpropyl)-3-oxo-cyclopentyl)acetate, isopropyl (2-pentyl-3-oxo-cyclopentyl) acetate, isopropyl (2-(2-pentenyl)-3-oxo-cyclopentyl) acetate, isopropyl (2-(3-pentenyl)3-oxo-cyclopentyl)acetate, butyl (2-pentyl-3-oxo-cyclopentyl)-acetate, butyl (2-(2-pentenyl)-3-oxo-cyclo-pentyl)acetate, butyl (2-(3-pentenyl) 3-oxo-cyclopentyl)-acetate, isobutyl (2-pentyl-3-oxo-cyclopentyl)acetate, isobutyl (2-(2-pentenyl)-3-oxo-cyclopentyl)acetate, sec-butyl (2-pentyl-3-oxo-cyclopentyl) acetate, sec-butyl (2-(2-pentenyl)-3-oxo-cyclopentyl) acetate, t-butyl (2-pentyl-3-oxo-cyclopentyl)-acetate, pentyl (2-pentyl-3-oxo-cyclopentyl)acetate, pentyl (2-(2-pentenyl)-3-oxo-cyclopentyl)acetate, 2-methylbutyl (2-pentyl-3-oxo-cyclopentyl)acetate, hexyl (2-pentyl-3-oxo-cyclopentyl)-acetate, hexyl (2-(2-pentenyl)-3-oxo-cyclopentyl)acetate, heptyl (2-(2-pentenyl)-3-oxo-cyclopentyl)acetate, octyl (2-pentyl-3-oxo-cyclopentyl)-acetate, octyl (2-(2-pentenyl)-3-oxo-cyclopentyl)acetate and decyl (2-pentyl-3-oxo-cyclopentyl)acetate. The jasmonic acid esters are not particularly limited to these examples. Of these, ethyl (2-pentyl-3-oxo-cyclopentyl)acetate, ethyl (2-(2-pentenyl)-3-oxo-cyclopentyl)acetate, propyl (2-pentyl-3-oxo-cyclopentyl)acetate, propyl (2-(2-pentenyl)-3-oxo-cyclopentyl)acetate, propyl (2-(3-pentenyl)-3-oxo-cyclopentyl)acetate, propyl (2-(2-methylbutyl)-3-oxo-cyclopentyl)acetate, propyl (2-(2,2-dimethylpropyl)-3-oxo-cyclopentyl)acetate, isopropyl (2-pentyl-3-oxo-cyclopentyl)-acetate, isopropyl (2-(2-pentenyl)-3-oxo-cyclopentyl)acetate, isopropyl (2-(3-pentenyl)-3-oxo-cyclopentyl)acetate, butyl (2-pentyl-3-oxo-cyclopentyl)-acetate, butyl (2-(2-pentenyl)-3-oxo-cyclopentyl)acetate, butyl (2-(3-pentenyl)-3-oxo-cyclopentyl) acetate, isobutyl (2-pentyl-3-oxo-cyclopentyl)-acetate, isobutyl (2-(2-pentenyl)-3-oxo-cyclopentyl)acetate, sec-butyl (2-pentyl-3-oxo-cyclopentyl)acetate, sec-butyl (2-(2-pentenyl)-3-oxo-cyclopentyl)acetate, t-butyl (2-pentyl-3-oxo-cyclopentyl)-acetate, pentyl (2-pentyl-3-oxo-cyclopentyl)acetate, pentyl (2-(2-pentenyl)-3-oxo-cyclopentyl)acetate, 2-methylbutyl (2-pentyl-3-oxo-cyclopentyl)acetate, hexyl (2-pentyl-3-oxo-cyclopentyl)-acetate, hexyl (2-(2-pentenyl)-3-oxo-cyclopentyl)acetate, heptyl (2-(2-pentenyl)-3-oxo-cyclopentyl)acetate, octyl (2-pentyl-3-oxo-cyclopentyl) -acetate and octyl (2- (2-pentenyl) -3-oxo-cyclopentyl) acetate are preferable. Propyl (2-pentyl-3-oxo-cyclopentyl) acetate, propyl (2-(2-pentenyl)-3-oxo-cyclopentyl)acetate, propyl (2-(3-pentenyl)-3-oxo-cyclopentyl)acetate, propyl (2-(2-methylbutyl)-3-oxo-cyclopentyl)acetate, propyl (2-(2,2-dimethylpropyl)-3-oxo-cyclopentyl)acetate, isopropyl (2-pentyl-3-oxo-cyclopentyl)-acetate, isopropyl (2-(2-pentenyl)- 3-oxo-cyclopentyl)-acetate, isopropyl (2-(3-pentenyl) -3-oxo-cyclopentyl)acetate, butyl (2-pentyl-3-oxo-cyclopentyl)-acetate, butyl (2-(2-pentenyl)-3-oxo-cyclopentyl)acetate, butyl (2-(3-pentenyl)-3-oxo-cyclopentyl)acetate, isobutyl (2-pentyl-3-oxo-cyclopentyl)-acetate, isobutyl (2-(2-pentenyl)-3-oxo-cyclopentyl)acetate, sec-butyl (2-pentyl-3-oxo-cyclopentyl)-acetate, sec-butyl (2-(2-pentenyl)-3-oxo-cyclopentyl)acetate and t-butyl (2-pentyl-3-oxo-cyclopentyl)acetate are especially preferable.

These jasmonic acid esters may be used either alone or as a combination of at least two thereof.

These jasmonic acid esters are prepared by the ordinary methods. For example, a jasmonic acid ester of the formula (1) wherein $R^1$ is a pentyl group and $R^2$is an alkyl group is prepared by a process wherein 2-pentylcyclopenten-1-on and an alkyl ester of malonic acid are subjected to Michael addition and the addition product is decarboxylated.

The ratio of gibberellin to the jasmonic acid ester in the plant growth regulator of the present invention varies depending upon the particular plant species, the effect and application procedure of the active ingredients and is not particularly limited, but the gibberellin/jasmonic acid ester ratio is usually in the range of 1/0.001 to 1/1,000,000, preferably 1/0.01 to 1/10,000, more preferably 1/0.05 to 1/1,000 and most preferably 1/0.1 to 1/100 by weight. When the ratio of gibberellin to the jasmonic acid ester is chosen within this range, a high synergistic effect for plant growth regulation can be obtained.

The above-mentioned two active ingredients for the plant growth regulator of the present invention are used usually in combination with at least one ingredient selected from a solid carrier, a liquid carrier and a dispersant.

The contents of gibberellin and the jasmonic acid ester in the plant growth regulator of the present invention are suitably chosen depending upon the particular plant species, the preparation form of the regulator, the procedure of application and the stage of plant development. For example, when the active ingredients are used in combination with a solid carrier, the content of gibberellin is usually in the range of 0.001 to 45% by weight, preferably 0.01 to 25% by weight and more preferably 0.1 to 10% by weight, based on the total weight of the plant growth regulator, and the content of the jasmonic acid ester is usually in the range of 0.001 to 45% by weight, preferably 0.01 to 25% by weight and more preferably 0.1 to 10% by weight, based on the total weight of the plant growth regulator. When the active ingredients are used in combination with a liquid carrier, the content of gibberellin is usually in the range of 0.001 to 45% by weight, preferably 0.01 to 25% by weight and more preferably 0.1 to 10% by weight, based on the total weight of the plant growth regulator, and the content of the jasmonic acid ester is usually in the range of 0.001 to 45% by weight, preferably 0.01 to 25% by weight and more preferably 0.1 to 10% by weight, based on the total weight of the plant growth regulator.

As preferable examples of the solid carrier, there can be mentioned inorganic materials such as kaolinite group, montmorillonite group, attapulgite group, clay group such as those which are represented by talc, mica, pyrophylite, pumice, vermiculite, gypsum, calcium carbonate, dolomite, diatomaceous earth, magnesium, calcium hydroxide, phosphorus lime, zeolite, silicic anhydride and synthetic calcium silicate; vegetable-based organic materials such as soybean powder, tobacco powder, walnut powder, wheat flour, wood flour, starch, crystalline cellulose, ester gum, copal gum and dammar gum; synthetic high polymeric substances such as cumarone resin, petroleum resin, alkyd resin, polyvinyl chloride, and a ketone resin; waxes such as carnauba wax and beeswax; and ureas. These solid carriers may be employed alone or in combination.

As preferable liquid carriers used, there can be mentioned paraffinic, naphthenic, and aromatic hydrocarbons such as kerosine, mineral oil, spindle oil and white oil, benzene, toluene, xylene, ethylbenzene, cumene and methylnaphthalene; chlorohydrocarbons such as carbon tetrachloride, chloroform, trichloroethylene, monochlorobenzene and o-chlorotoluene; ethers such as dimethyl ether, diethyl ether, dioxane and tetrahydrofuran; ketones such as acetone, methyl ethyl ketone, diethyl ketone, diisobutyl ketone, cyclopentanone, cyclohexanone, acetophenone and isophorone; esters such as ethyl acetate, amyl acetate, ethylene glycol acetate, diethylene glycol acetate, dibutyl maleate and diethyl succinate; alcohols such as methanol, ethanol, n-propanol, isopropanol, n-hexanol, ethylene glycol, diethylene glycol, and glycerine; ether-alcohols such as ethylene glycol phenyl ether and diethylene glycol butyl ether, and dimethylformamide and dimethylsulfoxide; and water. Of these, hydrocarbons, ketones, alcohols, and water are preferable, and alcohols and water are most preferable. These liquid carriers may be employed alone or in combination.

As the dispersant, surface active agents are usually used, which include nonionic, cationic, anionic and ampholytic surface active agents. In general a nonionic surface active agent is preferably used.

As specific examples of the nonionic surface active agent, there can be mentioned block co-polycondensates of at least two alkylene oxides such as an oxyethylene-oxypropylene block copolymer; polyoxyalkylene ether-type compounds which are prepared by addition polymerization of an alkylene oxide with a higher alcohol such as lauryl alcohol, cetyl alcohol, stearyl alcohol or oleyl alcohol, an alkylphenol such as octylphenol, isooctylphenol or isononylphenol, or an alkylnaphthol such as butylnaphthol or octylnaphthol, which include polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether and polyoxyethylene higher alcohol ($C_{12}$–$C_{14}$) ether; polyoxyalkylene glycol fatty acid ester-type compounds which are preapred by addition polymerization of an alkylene oxide with a higher fatty acid such as lauryl acid, palmitic acid, stearic acid or oleic acid, which include polyoxyethylene glycol monolaurate, polyoxyethylene glycol monopalmitate, polyoxyethyleneglycol monostearate, polyoxyeethylene glycol distearate and polyethylene glycol monooleate; polyhydric alcohol-type higher fatty acid ester compounds which are prepared by esterification of a polyhydric alcohol having at least three hydroxyl groups in the molecule, such as glycerin, pentaerythritol, sorbitol, sorbitan, mannitan, hexitan and polycondensates thereof, with a higher fatty acid, which include glyceryl monostearate, glyceryl monooleate, glyceryl monolaurate, sorbitol monopalmitate, sorbitol monostearate, sorbitol distearate, sorbitol tristearate, sorbitol monooleate, sorbitol dioleate, sorbitol trioleate, sorbitol tetraoleate, sorbitan monolaurate, sorbitan monopalmitate, sorbitan monostearate, sorbitan distearate, sorbitan tristearate, sorbitan monooleate, sorbitan dioleate, mannitan monolaurate, mannitan monostearate, mannitan distearate, mannitan monooleate, hexitan monolaurate, hexitan monopalmitate, hexitan monostearate, hexitan distearate, hexitan tristearate, hexitan monooleate and hexitan dioleate; polyoxyalkylene polyhydric alcohol-type fatty acid ester compounds, which are prepared by addition polymerization of the above-mentioned polyhydric alcohol-type fatty acid ester compound with an alkylene oxide, or by addition polymerization of the above-mentioned polyhydric alcohol-type fatty acid ester compound with an alkylene oxide, followed by esterification of the addition polymerization product with the above-mentioned higher fatty acid, and which include polyoxyethylene sorbitan monolaurate, polyoxyethylene sorbitan monostearate, polyoxyethylene sorbitan distearate, polyoxyethylene sorbitan monooleate, polyoxyethylene mannitan monopalmitate, polyoxyethylene mannitan monostearate, polyoxyethylene mannitan monooleate, polyoxyethylene hexitan monolaurate, polyoxyethylene hexitan monostearate and polyoxyethylene sorbitol tetraoleate; polyoxyalkylene alkylamine compounds such as polyoxyethylene alkylamine; and alkylalkanol amide compounds. Of these, block co-polycondensates of at least two alkylene oxides; and polyoxyalkylene-type compounds, i.e., addition polymerization products of an alkylene oxide such as polyoxyalkylene ether-type compounds, polyoxyalkylene glycol fatty acid ester-type compounds, polyoxyalkylene polyhydric alcohol-type fatty acid ester compounds and polyoxyalkylene alkylamine compounds are preferable. Polyoxyalkylene ether-type compounds, polyoxyalkylene glycol fatty acid ester-type compounds and polyoxyalkylene polyhydric alcohol-type fatty acid ester compounds are especially preferable.

These dispersants may be used either alone or as a combination of at least two thereof. The amount of the dispersant is usually in the range of 5 to 60% by weight, preferably 10 to 50% by weight and more preferably 15 to 45% by weight based on the total weight, in the case where any of a solid carrier or a liquid carrier is used.

If desired, the plant growth regulator of the present invention can be incorporated with conventional adjuvants such as a wetting agent, an anchorage (adhesive agent) and a disintegrant. If desired, the plant growth regulator of the present invention can be incorporated with plant hormones such as auxin, cytokinin, indol acetic acid, abscisic acid, ethylene and ethylene generator; a fungicide and a bacteriocide, an insecticide, a herbicide, an acaricide, a fungicide and a bacteriocide for agricultural and horicultural plants, a soil sterilizer, a soil conditioner and a nematocide, and the plant growth regulator of the present invention can be further incorporated with fertilizers or other plant growth regulators.

The form of preparation thereof is not particularly limited, and may be suitabley chosen by depending upon the form of the above-mentioned carrier, i.e., whether the carriesr is a solid or a liquid. For example, the active ingredients can be applied in the form of emulsions, suspensions, powders, wettable powders, wettable granules, dispersions, granules, pastes and aerosols.

The method for preparation of the plant growth regulator of the present invention is not particularly limited, and any of the heretofore known methods can be employed. For example, as specific example of the method for preparing a wettable powder, there can be mentioned a method wherein gibberellin or the jasmonic acid ester is dissolved or dispersed in a liquid carrier, a dispersant and/or a solid carrier is incorporated in the thus-prepared solution or dispersion, the resulting mixture is thoroughly stirred and, if desired, the liquid carrier is removed to obtain a wettable powder. As specific example of the method for preparing an emulsion, there can be mentioned a method wherein gibberellin or the jasmonic acid ester and a dispersant are mixed together with an alcoholic liquid carrier such as propanol to obtain an emulsion.

The plant growth regulator of the present invention can be applied directly onto a crop or a soil, but it is most effective that the plant growth regulator is diluted with or dispersed in water to obtain an aqueous liquid having a desired concentration, and the aqueous liquid is applied to a crop.

The preparation of the aqueous liquid can be conducted by an ordinary procedure. For example, the above-mentioned plant growth regulator, preferably composed of the two active ingredients, a liquid carrier and a dispersant, is diluted and mixed with water to prepare the aqueous liquid.

The content of gibberellin and the jasmonic acid ester in an aqueous medium varies depending upon the particular species of plants, the application form, the application procedure and the application stage. The content of gibberellin is usually in the range of 0.01 to 1,000 ppm, preferably 0.1 to 100 ppm, more preferably 0.1 to 80 ppm, and most preferably 1 to 40 ppm, and the content of jasmonic acid ester in the aqueous liquid is usually in the range of 0.01 to 1,000 ppm, preferably 0.1 to 500 ppm, more preferably 0.5 to 300 ppm, and most preferably 1 to 100 ppm. When the contents of the respective ingredients are within the specified ranges, the plant growth promoting effect develops efficiently.

Process for Regulating Plant Growth

The process for regulating plant growth of the present invention, is characterized in that gibberellin and a jasmonic acid ester represented by the above-mentioned general formula (1) are applied in combination to exhibits their effects. Therefore, in the process for regulating plant growth of the present invention, gibberellin and the jasmonic acid ester may be applied as a mixture to plants, or these active compounds may be applied to plants separately, i.e., by a procedure wherein, while the earlier applied one is still effective the other is applied to the plants. When gibberellin and the jasmonic acid ester are applied as a mixture, the above-mentioned plant growth regulator is used. When gibberellin and the jasmonic acid ester are applied to plants separately, single agents which contain one of the two compounds and the other, respectively, as an active ingredient are prepared, and, the single agents are applied concurrently or separately. When they are applied separately, their application order is not limited, but in a period in which the active ingredient in the earlier applied single agent is still effective, usually in one week, preferably in three days, and more preferably in two days, the other single agent can be applied. Since the persistence times of the respective single agents vary depending upon the particular kind of plant and the procedure of application, it is preferable to use the plant growth regulator of the present invention which is a mixture of the two active ingredients.

The concentration of gibberellin and the jasmonic acid ester, applied to plants, may be varied depending upon the particular kind of plant species, the effect of action, and the application procedure thereof. However, it is preferable that the concentration of these active ingredients are in the same level as that of aqueous medium in the plant growth regulator, to obtain a good regulation effect for plant growth.

The ratio of the jasmonic acid ester and gibberellin may be varied depending upon the particular species of crop, the effect of action and the application procedure. In order to obtain a high synergistic effect on the plant, it is preferable to adopt the same combination ratio as that described in the above-mentioned plant growth regulator.

As specific examples of the plant to which the regulator is applied, fruit vegetables such as cucumber, egg plant, green pepper, pumpkin and squash, water melon, oriental pickling melon (*Cucumis melo L.* var. *comonon MAKINO*), oriental melon (*Cucumis melo L.* var. *makuwa MAKINO*), musk melon, okura (*Abelmoschus esculentus MOENCH*), strawberry and tomato; fruit trees from which fruits are harvested such as grape, pear, apple, peach, sweet cherry, persimmon and mandarin orange; root vegetables from which roots are harvested, such as Japanese radish, carrot, turnip, edible burdock, table beet, potato, sweet potato, onion, taro and cassava; leaf vegetables from which leaves are harvested such as Chinese cabbage, cabbage, welsh onion, leek, cauliflower, parsley, Mitsuba (*Cryptotaenia japonica MAKINO*), celery, Garland chrysanthemum, spinach, lettuce, rape, and pot herb mustard; beans such as kidney bean, broad bean, pea, soybean, peanut and azuki bean; cereals such as rice, barley, wheat, oat, foxtail millet, barnyard millet, millet, buck wheat and corn; flowers and ornamental plants such as lily, tulip, gladiolus, carnation and rose; industrial crops such as cotton, hemp, sugar beet, turf and stevia; and wood plants such as Japanese cedar, cypress, pine and hiba arborvitae. The plants to which the plant growth regulator is applied are not limited to these recited plants. For example, the plant growth regulator of the present invention can be preferably used for fruit vegetables and fruit trees, root vegetables, leaf vegetables, beans, cereals, and flowers and ornamental plants. More preferably, the regulator gives its growth regulation effect for fruit trees, and most preferably, for grape.

As specific examples of the growth regulation action of the crop to which the plant growth regulator is applied, there can be mentioned rooting acceleration, germination acceleration, flowering acceleration, bloom acceleration, growth and development acceleration, seedless fruitage, fruiting ratio improvement, fruit enlargement, maturation period acceleration, coloring improvement, sweetness enhancement, and fruit drop control. Of these, the regulator is applied preferably for germination acceleration, bloom acceleration, growth and development acceleration, seedless fruitage, fruit enlargement, and maturation period acceleration, more preferably for germination acceleration, seedless fruitage, and fruit enlargement.

As application sites for plant systems at which the plant growth regulator of the present invention is applied vary depending upon the particular kind of plants or intended effect, but usually it is applied on seeds, flower buds (flower cluster), fruit (fruit cluster), leaves, stems, roots, tubers, and rhizomes. For example, the application on seeds induces the action of germination acceleration or growth and development acceleration, and that on flower buds or flower buds precursor sites usually induces the action of bloom acceleration or flowering acceleration. The application on flowers or flower clusters usually induces the action of seedless fruitage, enhancement of number of set fruit, or fruit enlargement, and that on fruits or fruit clusters induces fruit enlargement, maturation period acceleration, coloring improvement, sweetness enhancement, and fruit drop control. The application onto leaves, stems, roots or tubers usually induces the effect of growth and development acceleration.

As the most effective application sites are as follows: seeds of crops such as leaf vegetables, beans and cereals for germination acceleration; leaves or stems of plants such as root vegetables, leaf vegetables, beans, cereals for growth and development acceleration; flower buds or flower buds precursor sites of flowers and ornamental plants for bloom acceleration; flowers or flower clusters of fruit vegetables for seedless fruitage; flower or flower clusters and fruit or fruit clusters of fruit vegetables for fruit enlargement, and so forth.

A preferable procedure by which the plant growth regulator is applied varies depending upon the particular crop plant species, or the action and effect, and the following procedures are employed: dipping of seeds, seed tubers, flower buds, flowers, flower clusters, fruits, fruit clusters in a liquid preparation; spraying a liquid preparation onto foliage, or fruit surface; drenching the liquid preparation on soil; and injecting the liquid preparation into plant lives.

The dipping time of seeds or seed tubers in the liquid preparation is appropriately determined depending upon the crop species, but in general, it is several seconds to several days, preferably 1 to 48 hours, more preferably 6 to 12 hours. The dipping times for flower buds, flowers, flower clusters, fruits, or fruit clusters are selected from the range of one moment to several ten minutes, preferably 1 to 30 seconds, more preferably several seconds.

The number of application is not limited, and the application is usually conducted at one time to several times.

Preferable activities of the plant growth regulator of the present invention are summarized as follows.

(1)Acceleration of Germination

The effect of acceleration of germination is manifested on various plants which include preferably fruit vegetables, root vegetables, leaf vegetables, beans and cereals, and more preferably root vegetables, beans and cereals. The procedure of application is not particularly limited, but is preferably a dipping procedure of seeds. The dipping of seeds is effected by dipping seeds in a liquid containing the active ingredients at the concentration as described above with reference to the aqueous preparation for usually 0.1 to 48 hours, preferably 1 to 24 hours and more preferably 6 to 12 hours.

(2) Bloom Acceleration

The effect of bloom acceleration is manifested on, for example, fruit vegetables, leaf vegetables, and flower and ornamental plants, and markedly manifested on plants for which a chilling treatment or a long-day treatment is required for bloom, such as, for example, strawberry and spinach. Further, the effect of bloom acceleration is markedly manifested on flowers and ornamental plants cultivated in green houses such as, for example, carnation, *Tanacetum*

*pathenium, Sch. Bip., cyclamen, primura* and *Gymnaster savatieri kitam*. The application is conducted usually by atomizing the liquid on the plant live before flower bud differentiation.

(3) Growth and Development Acceleration

The effect of growth and development acceleration is manifested on various plants which include preferably fruit vegetables, root vegetables, leaf vegetables, beans and cereals, and more preferably leaf vegetables, root vegetables and beans. The application is effected usually by foliar-spraying the liquid on a young plant with 2 to 6 leaves, or a plant one to five weeks, preferably about 2 or 3 weeks, before the harvest.

(4) Seedless Fruitage and Fruit Enlargement

The effect of fruit enlargement is manifested on fruits, preferably fruit trees and more preferably grape. The kind of grape is not particularly limited, and various kinds of grape are included. As specific examples of the grape, there can be mentioned Delaware, Kyohou, Pione, muscat berry A, muscat of Alexandria, neomuscat, Koshu, Himrod, Hiro-Hamburg, Cambell early, Niagara and Takao.

The effect of seedless fruitage is obtained by applying the plant growth regulator to flower clusters at one or more times in a stage spanning from 4 weeks before the full bloom to the full bloom, preferably about 1 to 3 weeks before the full bloom and more preferably about 2 weeks before the full bloom.

The effect of fruit enlargement is effected by applying the plant growth regulator to flowers or fruits, especially flower clusters of grape (which means flowers occurring closely together in a tuf ty form and being in a stage spanning from flower bud to termination of bloom, i.e., to completion of falling of all corollas, and fruit clusters thereof. When the plant growth regulator is applied to flower clusters, the application is conducted at least one time in a stage spanning from the beginning of bloom to the termination of bloom, preferably to about 4 weeks after the full bloom, more preferably in 1 to 3 weeks after the full bloom, and most preferably about 2 weeks after the full bloom.

When the plant growth regulator is applied for the purpose of both seedless fruitage and fruit enlargement, the application is conducted to flower clusters of grape at least one time in a stage spanning from 4 weeks before the full bloom to the full bloom, preferably in a stage of about 1 to 3 weeks before the full bloom, and further at least one time in a stage spanning from the full bloom to about 4 weeks after the full bloom, preferably in a stage of 1 to 3 weeks after the full bloom, and more preferably about 2 weeks after the full bloom. The application is effected by a procedure wherein the flower clusters or fruit clusters are dipped in a liquid containing the active ingredients at the concentration mentioned above with reference to the aqueous liquid, or a procedure wherein the active ingredient-containing liquid is atomized onto flower clusters, fruit clusters or the entire plants. The dipping of flower clusters is preferable.

(5) Acceleration of Maturation Period

The acceleration of maturation period leads to sweetness enhancement, flower acceleration and other effects, as well as hastening of harvest stage. The effect of acceleration of matured period is remarkably manifested on fruits, preferably fruit trees and more preferably grape. The application is effected by a procedure of dipping flower clusters or fruit clusters in the active ingredient-containing liquid or a procedure of atomizing the active ingredient-containing liquid on clusters or fruit clusters. The dipping procedure is preferable. The stage of application is usually 1 to 5 weeks before the harvest, and preferably 2 to 4 weeks before the harvest.

The invention will now be described specifically by the following examples, but should not be construed to be limited thereto.

Preparation of Testing Liquids

Gibberellin or the jasmonic acid ester of formula (1) was incorporated in a mixed liquid composed of n-propanol/water/polyoxyethylene sorbitan monooleate (weight ratio=35/35/30) to obtain an aqueous emulsion containing 5% by weight of the active ingredients. The aqueous emulsion was diluted with water to prepare a testing liquid containing the active ingredients at the concentration shown in Table 1 and Table 2. A mixed liquid composed of n-propanol/water/polyoxyethylene sorbitan monooleate and not containing gibberellin nor the jasmonic acid ester was prepared and diluted with 1,000 times of water to prepare a control testing liquid (testing liquid No. 1 in Table 1).

TABLE 1

| Test liquid | Gibberellin conc.(ppm) | | Jasmonate | | |
|---|---|---|---|---|---|
| No. | GA3 | GA4 | $R^{1**}$ | $R^{2**}$ | conc. (ppm) |
| 1* | — | — | — | — | — |
| 2 | 5 | — | — | — | — |
| 3 | 10 | — | — | — | — |
| 4 | 25 | — | — | — | — |
| 5 | 30 | — | — | — | — |
| 6 | 100 | — | — | — | — |
| 7 | — | 5 | — | — | — |
| 8 | — | 10 | — | — | — |
| 9 | — | — | pentyl | methyl | 5 |
| 10 | — | — | pentyl | ethyl | 5 |
| 11 | — | — | pentyl | propyl | 2 |
| 12 | — | — | pentyl | propyl | 5 |
| 13 | — | — | pentyl | propyl | 10 |
| 14 | — | — | pentyl | propyl | 25 |
| 15 | — | — | pentyl | isopropyl | 5 |
| 16 | — | — | pentyl | butyl | 5 |
| 17 | — | — | pentyl | hexyl | 5 |
| 18 | — | — | pentenyl | methyl | 5 |
| 19 | — | — | pentenyl | propyl | 5 |
| 20 | — | — | pentenyl | butyl | 5 |

*1/1000 diluted solution of the mixture comprising n-propanol : $H_2O$ : polyoxyethylenesorbitan monooleate = 35 : 35 : 30 (by weight)
**$R^1$ and $R^2$ occur in the above-mentioned formula (1)

TABLE 2

| Test liquid | Gibberellin conc.(ppm) | | Jasmonate | | |
|---|---|---|---|---|---|
| No. | $GA_3$ | $GA_4$ | $R^{1**}$ | $R^{2**}$ | conc.(ppm) |
| 21 | 5 | — | pentyl | methyl | 5 |
| 22 | 5 | — | pentyl | ethyl | 5 |
| 23 | 5 | — | pentyl | propyl | 2 |
| 24 | 10 | — | pentyl | propyl | 2 |
| 25 | — | 10 | pentyl | propyl | 2 |
| 26 | 5 | — | pentyl | propyl | 5 |
| 27 | 10 | — | pentyl | propyl | 5 |
| 28 | 25 | — | pentyl | propyl | 5 |
| 29 | — | 5 | pentyl | propyl | 5 |
| 30 | — | 10 | pentyl | propyl | 5 |

TABLE 2-continued

| Test liquid | Gibberellin conc.(ppm) | | Jasmonate | | |
|---|---|---|---|---|---|
| No. | $GA_3$ | $GA_4$ | $R^{1**}$ | $R^{2**}$ | conc.(ppm) |
| 31 | 5 | — | pentyl | propyl | 10 |
| 32 | 10 | — | pentyl | propyl | 10 |
| 33 | 25 | — | pentyl | propyl | 10 |
| 34 | 30 | — | pentyl | propyl | 10 |
| 35 | 5 | — | pentyl | propyl | 25 |
| 36 | 10 | — | pentyl | propyl | 25 |
| 37 | 25 | — | pentyl | propyl | 25 |
| 38 | 5 | — | pentyl | isopropyl | 5 |
| 39 | 5 | — | pentyl | butyl | 5 |
| 40 | 5 | — | pentyl | hexyl | 5 |
| 41 | 5 | — | pentenyl | methyl | 5 |
| 42 | 5 | — | pentenyl | propyl | 5 |
| 43 | 10 | — | pentenyl | propyl | 5 |
| 44 | — | 10 | pentenyl | propyl | 5 |
| 45 | 5 | — | pentenyl | butyl | 5 |
| 46 | 10 | — | abscisic acid | | 2 |

$R^1$ and $R^2$ occur in the above-mentioned formula (1)

EXAMPLES 1 TO 9 AND COMPARATIVE EXAMPLES 1 to 10

Growth and Development Acceleration Effect on Spinach

Seeds of spinach (variety: Echijirou-maru) were sowed in an outdoor field, and 20 plants per testing zone were cultivated in the conventionally controlled manner. The testing liquid shown in Table 3 was sprayed in an amount of 20 milli-liters per testing zone at a stage of four true leaves. 35 days after the spraying, all of the plants were harvested at one time. Average individual weight was measured, and the ratio in % of the live weight to that as measured on control plants cultivated with the control testing liquid was calculated. The results are shown in Table 3.

TABLE 3

| | Example | | | | | | | | | |
|---|---|---|---|---|---|---|---|---|---|---|
| | 1 | 2 | 3 | 4 | 5 | 6 | 7 | 8 | 9 | |
| Test liquid No. | 21 | 22 | 26 | 38 | 39 | 40 | 41 | 42 | 45 | |
| GD acceleration* | 120 | 125 | 145 | 132 | 135 | 129 | 120 | 136 | 132 | |
| | Comparative Example | | | | | | | | | |
| | 1 | 2 | 3 | 4 | 5 | 6 | 7 | 8 | 9 | 10 |
| Test liquid No. | 9 | 10 | 12 | 15 | 16 | 17 | 18 | 19 | 20 | 2 |
| GD acceleration* | 105 | 109 | 117 | 110 | 115 | 108 | 105 | 110 | 108 | 110 |

*Growth and development acceleration effect

As seen from Table 3, when gibberellin and the jasmonic acid ester are applied in combination according to the present invention (Examples 1 to 9), good growth and development acceleration effect can be obtained. Especially when gibberellin is used in combination with a jasmonicacid ester wherein $R^2$ in formula (1) has at least 2 carbon atoms, a synergistic effect can be obtained. When the number of carbon atoms in $R^2$ is in the range of 2 to 6, a high synergistic effect is manifested (Examples 2 to 6 and 8 to 9), and, when the number of carbon atoms in $R^2$is 3 or 4, a much higher synergistic effect is manifested (Examples 3 to 5 and 8 to 9).

EXAMPLES 10 TO 13 AND COMPARATIVE EXAMPLES 11 to 14

Growth and Development Acceleration Effect on Radish

Radish (variety: Akamaru-comet) was cultivated in a conventional manner in outdoor fields at 20 plants per testing zone. The testing liquid shown in Table 4 was sprayed in an amount of 20 milli-liters per testing zone at a stage of four true leaves. One month after the spraying, all of the plants were harvested at one time. Average individual weight was measured, and the ratio in % of the live weight to that as measured on control plants cultivated with the control testing liquid. The results are shown in Table 4.

TABLE 4

| | Example | | | | Comparative Example | | | |
|---|---|---|---|---|---|---|---|---|
| | 10 | 11 | 12 | 13 | 11 | 12 | 13 | 14 |
| Test liquid No. | 27 | 43 | 30 | 44 | 3 | 8 | 12 | 19 |
| RD acceleration* | 128 | 124 | 127 | 121 | 105 | 107 | 111 | 109 |

*Root growth and development acceleration effect

As seen from Table 4, when $GA_3$ or $GA_4$ is used as gibberellin and a jasmonic acid ester wherein $R^1$ is a pentyl group and $R^2$ is a propyl group in formula (1) is used in combination according to the present invention (Examples 10 to 13), excellent growth acceleration is obtained on the root of radish and this growth acceleration effect is synergistic.

EXAMPLES 14 TO 22 AND COMPARATIVE EXAMPLES 15 to 21

Fruit Enlargement Effect on Grape (variety: Kyohou)

Grape tree (variety: Kyoho) with age of 20 was cultivated in a conventional manner and used for the test. 15 days after the full bloom, the flower clusters were dipped in the testing liquid shown in Table 5 for several seconds (20 flower clusters per each test zone). In the fruit maturation period, the fruits of grape were harvested at one time, and the average berry weight was measured. The ratio in % of the average berry weight to the average berry weight as measured on control grape cultivated without application of the testing liquid was calculated. The results are shown in Table 5.

TABLE 5

| | Example | | | | | | | | |
|---|---|---|---|---|---|---|---|---|---|
| | 14 | 15 | 16 | 17 | 18 | 19 | 20 | 21 | 22 |
| Test liquid No. | 25 | 26 | 27 | 30 | 31 | 32 | 34 | 35 | 36 |
| FE acceleration* | 120 | 133 | 125 | 122 | 128 | 127 | 120 | 123 | 124 |

| | Comparative Example | | | | | | |
|---|---|---|---|---|---|---|---|
| | 15 | 16 | 17 | 18 | 19 | 20 | 21 |
| Test liquid No. | 2 | 3 | 4 | 6 | 12 | 13 | 14 |
| FE acceleration* | 103 | 107 | 108 | 110 | 108 | 115 | 112 |

*Fruit enlargement effect

As seen from Table 5, in Examples 14 to 22 of the invention, excellent fruit enlargement effect is manifested on grape and the effect is synergistic. Further, the fruit enlargement effect obtained in Examples 14 to 22 is much higher than that of Comparative Example 18, although the concentration of gibberellin in Examples 14 to 22 is only 5 or 10 ppm whereas the concentration thereof in the comparative example is 100 ppm. Obviously very high gibberellin reducing effect and fruit enlargement effect are obtained, which are not obtained by the single use of gibberellin.

EXAMPLE 23 AND COMPARATIVE EXAMPLES 22 to 24

Seedless Fruitage of Grape Fruit

Grape tree (variety: Pione) with age of 13 was used for the test. Thinning was conducted so that each fruit bearing cane (current cane) had one flower cluster and each flower cluster had 40 to 45 berries. The trees having uniform branch lengths and stages were used for the test. Using the testing liquids shown in Table 6, the treatment with the solutions was conducted at a fine day in the optimum stage (15 days before the expected full bloom; the actual full bloom was 13 to 14 days after the treatment). One unit experiment was conducted in six testing zones each having 15 flower clusters. Each testing liquid was placed in a beaker and the flower clusters were dipped one by one in the testing liquid and shaken several times. The dipping time was about 3 seconds per flower cluster. 68 days after the dipping treatment with the solutions, the fruits were harvested at one time, and the seedless fruitage was evaluated. The percentage of seedless fruitage was calculated according to the following formula. The results are shown in Table 6.

Percentage of seedless fruitage=(number of seedless berries/total number of berries)×100

TABLE 6

| | Example | Comparative Example | | |
|---|---|---|---|---|
| | 23 | 22 | 23 | 24 |
| Test liquid No. | 32 | 3 | 13 | 1 |
| Seedless fruitage(%) | 98 | 73 | 41 | 30 |

As seen from Table 6, in the test of the invention (Example 23), the plant growth regulator exhibits a high seedless fruitage effect on grape, and this effect is synergistic.

EXAMPLE 24 AND COMPARATIVE EXAMPLES 25, 26

Growth and Enlargement Acceleration of Tomato Fruits

The growth and enlargement acceleration effect on tomato fruits were tested on tomatoes (variety: Momotarou) cultivated in a warmed greenhouse. When tomato fruits were enlarged to a size of about 4 cm, fruit thinning was conducted to an extent such that each fruit cluster had uniformly grown three fruits. The testing liquid shown in Table 7 was sprayed in an amount of 10 milli-liters per each fruit cluster. The test was conducted on 10 fruit clusters each having 3 fruits in each testing zone. When coloring commenced, the fruits were harvested and weighed. An average fruit weight was measured on 30 tomatoes in each testing zone. The ratio in % of the average fruit weight to the average fruit weight as measured on control tomatoes cultivated without application of the testing liquid was calculated. The results are shown in Table 7. As seen from Table 7, in the test of the invention (Example 24), the plant growth regulator exhibits an excellent fruit enlargement effect on tomato, and this effect is synergistic.

TABLE 7

| | Example | Comparative Example | |
|---|---|---|---|
| | 24 | 25 | 26 |
| Test liquid No. | 34 | 5 | 13 |
| Fruit enlargement(%) | 131 | 109 | 115 |

EXAMPLES 25, 26 AND COMPARATIVE EXAMPLES 27 to 29

Enhancement of Number of Set Grains of Paddy Rice

Twenty seedlings of paddy rice (variety: Nippon-bare) per testing zone were cultivated in a conventional manner. The testing liquid shown in Table 8 was sprayed in an amount of 10 liters/are at young ear-forming stage. The average number of grains per each ear was measured in the harvest season. The ratio in % of the average number of grains to that as measured on control paddy rice grown without the spray-treatment with the testing liquid was calculated. The results are shown in Table 8. As seen from Table 8, in Examples 25 and 26 of the invention, the plant growth regulator exhibits excellent and synergistic enhancement effect of set grain number of paddy rice.

TABLE 8

| | Example | | Comparative Example | | |
|---|---|---|---|---|---|
| | 25 | 26 | 27 | 28 | 29 |
| Test liquid No. | 24 | 25 | 3 | 8 | 11 |
| GNE effect* | 109 | 112 | 102 | 104 | 102 |

*Grain number enhancement effect

EXAMPLE 27 AND COMPARATIVE EXAMPLES 30, 31

Germination-Promotion of Paddy Rice

Germination test of seeds of paddy rice (variety: Koshihikari) were conducted as follows. The seeds of pady rice were dipped in the testing liquid shown in Table 9 for two hours. The thus-treated seeds were sowed directly in a paddy field at a water temperature of 15 to 16° C. 13 days after the sowing, the germination percentage was measured. The ratio in % of the germination percentage to that as measured on control seeds of paddy rice sowed without the dipping treatment with the testing liquid was calculated. The results are shown in Table 9. As seen from Table 9, in Example 27 of the invention, a very high germination percentage can be obtained by the dipping treatment of seeds with the liquid of the plant growth regulator.

TABLE 9

| | Example | Comparative Example | |
|---|---|---|---|
| | 27 | 30 | 31 |
| Test liquid No. | 24 | 3 | 11 |
| Germination acceleration Effect | 293 | 137 | 183 |

EXAMPLES 28, 29 AND COMPARATIVE EXAMPLES 32 TO 34

Acceleration of Blooming of Petunia 10 seedlings of petunia (variety: hybrid of petunia with Titan) per each testing zone were cultivated. The testing liquid shown in Table 10 was sprayed in an amount of 50 milli-liters per each zone at a stage of 10 to 12 true leaves, i.e., in the latter part of February. The thus-treated plants were cultivated under open field conditions. The day on which blooming commenced was examined on five individuals in each testing zone. Number of days, by which the blooming was earlier than the average blooming-commencing days as examined on control plants cultivated without the spray treatment with the testing liquid, are shown in Table 10. As seen from Table 10, in Examples 28 and 29 of the invention, excellent and synergistic blooming acceleration effect is manifested.

TABLE 10

| | Example | | Comparative Example | | |
|---|---|---|---|---|---|
| | 28 | 29 | 32 | 33 | 34 |
| Test liquid No. | 24 | 25 | 3 | 8 | 11 |
| Blooming acceleration effect | 15 | 18 | 6 | 7 | 5 |

EXAMPLE 30 AND COMPARATIVE EXAMPLES 35 TO 37

Enhancement of Number of Wheat Ears

Six seeds of fall seeding wheat (variety: Bezostaja 1) were sowed in each pot [(1/5,000) are] at the beginning of November, and cultivated under open field conditions. Thinning was conducted in February to leave three uniform plants in each pot. When growth commenced in early spring at the beginning of March, the testing liquid shown in Table 11 was sprayed in an amount of 5 ml per each pot. In the harvest season, the number of ears was counted, and the ratio in % of the number of ears to that as counted on wheat grown without the treatment with the testing liquid was calculated. The results are shown in Table 11. As seen from Table 11, in the test of the invention (Example 30), an excellent effect on an increase of the number of ears is manifested, and this effect is synergistic.

TABLE 11

| | Example | Comparative Example | | |
|---|---|---|---|---|
| | 30 | 35 | 36 | 37 |
| Test liquid No. | 24 | 3 | 11 | 46 |
| EN enhancement effect* | 133 | 107 | 108 | 117 |

*Ear number enhancement effect

EXAMPLE 31 AND COMPARATIVE EXAMPLES 38, 39

Enhancement of Number of Wheat Ears

Six seeds of fall seeding wheat (variety: Banatka) were sowed in each pot [(1/5,000) are] at the beginning of November, and cultivated under open field conditions. Thinning was conducted in February to leave three uniform plants in each pot. When growth commenced in early spring at the beginning of March, the testing liquid shown in Table 12 was sprayed in an amount of 5 ml per each pot. In the harvest season, the number of ears was counted, and the ratio in % of the number of ears to that as counted on control wheat grown without the treatment with the testing liquid was calculated. The results are shown in Table 12. As seen from Table 12, in the test of the invention (Example 31), an excellent ear number-increasing effect on wheat is manifested, and this effect is synergistic.

TABLE 12

| | Example | Comparative Example | |
|---|---|---|---|
| | 31 | 38 | 39 |
| Test liquid No. | 24 | 3 | 11 |
| EN enhancement effect* | 134 | 106 | 1* + 07 |

*Ear number enhancement effect

Industrial Applicability

By applying gibberellin in combination with the jasmonic acid ester according to the present invention, the optimum amount of gibberellin can be reduced, and an excellent plant growth regulating effect is achieved which cannot be achieved by the single use of the active ingredients. The combined use of gibberellin with the jasmonic acid ester have enhanced beneficial effects which are manifested by gibberellin, such as rooting acceleration, germination acceleration, flowering acceleration, bloom acceleration, seedless fruitage, fruiting ratio improvement, fruit enlargement, maturation period acceleration, coloring improvement, sweetness enhancement and fruit drop control.

What is claimed is:

1. A plant growth regulator comprising, as the active ingredients, gibberellin and a jasmonic acid ester, represented by the following formula (1):

(1)

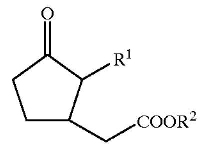

wherein $R^1$ and $R^2$ represent hydrocarbon groups, at a gibberellin/jasmonic acid ester ratio in the range of 1/0.001 to 1/1,000,000 by weight.

2. The plant growth regulator according to claim 1 wherein gibberellin is $GA_3$ or $GA_4$.

3. The plant growth regulator according to claim 1 wherein $R^1$ in formula (1) is an alkyl group having 1 to 20 carbon atoms, or an alkenyl group having 2 to 20 carbon atoms, and $R^2$ in formula (1) is an alkyl group having 1 to 20 carbon atoms.

4. The plant growth regulator according to claim 1, which further comprises at least one component selected the group consisting of a solid carrier, a liquid carrier, and a dispersant.

5. The plant growth regulator according to claim 1, which is in the form of an aqueous liquid diluted with water.

6. The plant growth regulator according to claim 5, wherein the content of gibberellin is 0.01 to 1,000 ppm in the aqueous liquid, and that of the jasmonic acid ester is 0.01 to 1,000 ppm in the aqueous liquid, respectively.

7. A process for regulating plant growth comprising applying to crops a synergistically effective amount of gibberellin in combination with a jasmonic acid ester represented by the following formula (1):

(1)

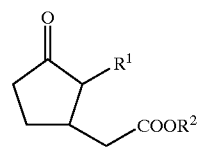

wherein $R^1$ and $R^2$ represent hydrocarbon groups.

8. The method according to claim 7 which results in a plant growth regulation effect selected from the group consisting of rooting acceleration effect, germination acceleration effect, flower acceleration effect, bloom acceleration effect, growth and development acceleration effect, seedless fruitage effect, fruiting ratio enhancement effect, fruit enlargement effect, maturation period acceleration effect, coloring improvement effect, sweetness enhancement effect and fruit drop control effect.

9. The method according to claim 8, wherein the plant growth regulation effect is fruit enlargement.

10. The method according to claim 8, wherein the plant growth regulation effect is seedless fruitage.

11. The method according to claim 7 wherein said gibberellin in combination with said jasmonic acid ester are applied to a plant selected from the group consisting of fruit vegetables, fruit trees, root vegetables, leaf vegetables, beans, cereals, flower and ornamental plants, industrial plants, and wood plants.

12. A process for regulating plant growth comprising applying to crops a plant growth regulator comprising gibberellin in combination with a jasmonic acid ester represented bv the following formula (1):

(1)

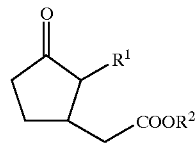

wherein $R^1$ and $R^2$ represent hydrocarbon groups, wherein the plant growth regulator described in any of claims 1 to 10 is used as a mixture of gibberellin and the jasmonic acid ester.

13. The process for regulating plant growth according to claim 7, wherein single agents comprising gibberellin or the jasmonic acid ester are applied separately to crops by a procedure wherein, while the earlier applied one is still effective, the other is applied.

14. The process for regulating plant growth according to claim 13, wherein the single agents are in the form of an aqueous liquid containing 0.01 to 1,000 ppm of gibberellin and an aqueous liquid containing 0.01 to 1,000 ppm of the jasmonic acid ester.

15. The process for regulating plant growth according to claim 7, wherein the ratio of gibberellin to the jasmonic acid ester is in the range of 1/0.001 to 1/1,000,000 by weight.

16. The process for regulating plant growth according to claim 7, wherein gibberellin and the jasmonic acid ester are applied to a seed, a flower bud, a flower, a flower cluster, a fruit, a fruit cluster, a leaf, a stem, a root or a tuber.

17. The process for regulating plant growth according to claim 7, wherein gibberellin and the jasmonic acid ester are applied by dipping or spraying.

18. The process for regulating plant growth according to claim 7, wherein gibberellin and the jasmonic acid ester are applied to a flower or a fruit of grapes by dipping or spraying to manifest a fruit enlargement effect.

19. The process for regulating plant growth according to claim 7, wherein gibberellin and the jasmonic acid ester are applied to a flower of grape by dipping or spraying to manifest a seedless fruitage effect.

20. The process for regulating plant growth according to claim 18, wherein gibberellin and the jasmonic acid ester are applied at one or more times in a stage spanning from four weeks before the full bloom to four weeks after the full bloom.

* * * * *